United States Patent [19]
Rowland

[11] Patent Number: 4,779,446
[45] Date of Patent: Oct. 25, 1988

[54] OXYGEN MONITOR

[75] Inventor: Robert O. Rowland, Hemet, Calif.

[73] Assignee: Hudson Oxygen Therapy Sales Company, Temecula, Calif.

[21] Appl. No.: 107,939

[22] Filed: Oct. 13, 1987

Related U.S. Application Data

[63] Continuation of Ser. No. 754,244, Jul. 12, 1985, abandoned.

[51] Int. Cl.$^4$ .................... G01N 27/26; G01D 18/00
[52] U.S. Cl. .......................................... 73/1 R; 73/1 G; 204/1 T; 204/401; 204/407; 204/431
[58] Field of Search ............. 73/1 G, 1 R, ; 340/514; 364/571; 204/401, 407, 434, 431, 1 T, 1 Y, 1 S, 1 P

[56] References Cited
U.S. PATENT DOCUMENTS

| | | | |
|---|---|---|---|
| 4,109,505 | 8/1978 | Clark et al. | 73/1 R |
| 4,189,725 | 2/1980 | Rowland | 340/636 |
| 4,322,964 | 4/1982 | Melguard et al. | 73/1 G |
| 4,331,862 | 5/1982 | Ryan | 73/1 R X |
| 4,367,133 | 1/1983 | Lauer | 204/25 X |
| 4,473,458 | 9/1984 | Schwartz et al. | 73/1 R X |
| 4,521,769 | 6/1985 | Dudeck et al. | 73/1 R X |

Primary Examiner—Tom Noland
Attorney, Agent, or Firm—John E. Wagner; Jerry R. Seiler

[57] ABSTRACT

The present invention is an improved method and apparatus for condition sensing and displaying a numeric value associated with the sensed condition wherein the improvement comprises (1) circuitry calibrating the display of the numerical value associated with the sensed condition to a numerical value associated with the sensed condition in a normal ambient environment, while the sensor is within the normal ambient environment; and (2) circuitry for calibrating the display of the numerical value of the sensed condition to a numerical value associated with the sensed condition in a known offset environment which is different than the normal ambient environment, while the sensor is in the known offset environment. The calibration of the display of the numerical value associated with the sensed condition in the normal ambient environment and in the known offset environment aiding in protection from a slope error condition and an offset error condition in the display of the numerical value associated with the sensed condition. The calibration circuitry includes switching elements and a microprocessor. In the exemplary embodiment the sensor is an electrochemical oxygen sensor, the normal ambient environment is open air, which contains 21% oxygen, and the known offset environment is pure oxygen. A system for monitoring battery supply is also included.

13 Claims, 9 Drawing Sheets

OXYGEN MONITOR

This application is a continuation of application Ser. No. 754,244 filed July 12, 1985 and now abandoned.

BACKGROUND OF THE INVENTION

The present invention relates to an improvement to the invention described in U.S. Pat. No. 4,189,725.

The present invention, similar to the previous invention described in U.S. Pat. No. 4,189,725, is an apparatus and method for sensing and displaying a numerical value associated with a condition which requires the interconnection of a sensing device which can sense the condition and produce an electrical signal proportional to the sensed condition. The condition which the preferred embodiment of the present invention is intended to display is the percentage of oxygen in the environment surrounding the sensing device. However, the present invention can be used to sense any condition where a sensing device can produce an electrical signal proportional to the condition to be sensed.

The present invention differs from the invention described in U.S. Pat. No. 4,189,725 by adding an improved apparatus and method for calibrating which corrects for both offset and slope error conditions, and, by adding an improved apparatus and method for monitoring batteries to insure that the accuracy and reliability of present invention is not compromised because the batteries are wearing out.

SUMMARY OF THE INVENTION

The present invention relates to a method and apparatus for condition sensing and displaying a numeric value associated with the sensed condition generally comprising (1) a sensor means for producing an electrical signal proportional to a sensed condition, (2) means for converting the electrical signal from the sensor means to digital signals, and (3) means responsive to the digital signals for displaying a numerical value associated with the sensed condition. The present invention is an improved method and apparatus comprising (1) means for calibrating the display of the numerical value associated with the sensed condition to a numerical value associated with the sensed condition in a normal ambient environment, while the sensor means is within the normal ambient environment; and, (2) means for calibrating the display of the numerical value of the sensed condition to a numerical value associated with the sensed condition in a known offset environment which is different than the normal ambient environment, while the sensor means is in the known offset environment. The calibration of the display of the numerical value associated with the sensed condition in the normal ambient environment and in the known offset environment aiding in protection from a slope error condition and an offset error condition in the display of the numerical value associated with the sensed condition.

The present invention also relates to an apparatus which uses a battery supply providing battery voltage and current to the apparatus and which comprises (1) means for monitoring the voltage of the battery supply, and (2) means for indicating when the battery supply voltage has dropped below a predetermined level. The present invention is an improved method and apparatus comprising (1) comparing means responsive to the means for monitoring the battery voltage for comparing the monitored battery voltage against average discharge information for the battery supply recommended for the apparatus, (2) estimated battery life calculating means responsive to the comparing means for calculating the estimated battery life of the battery supply after receiving a prompt to do so, (3) estimated battery life display means responsive to the estimated battery life calculating means for displaying the estimated battery life of the battery supply after receiving a prompt to do so, (4) means for manually prompting the estimated battery life display means, and, (5) means for automatically and periodically prompting the estimated battery life calculating means.

DETAILED DESCRIPTION OF THE INVENTION

The present invention is an improvement to the invention described in U.S. Pat. No. 4,189,725, which is incorporated herein by this reference as if fully set forth.

The present invention, similar to the pevious invention described in U.S. Pat. No. 4,189,725, is an apparatus and method for sensing and displaying a numerical value associated with a condition and requires the interconnection of a sensing device which can sense the condition and produce an electrical signal proportional to the sensed condition. The condition which the preferred embodiment of the present invention is intended to display is the percentage of oxygen in the environment surrounding the sensing device. However, the present invention can be used to sense any condition where a sensing device can produce an electrical signal proportional to the condition to be sensed.

The present invention differs from the invention described in U.S. Pat. No. 4,189,725 by the addition of an improved apparatus and method for calibration which corrects for both offset and slope error conditions, and, by the addition of an improved apparatus and method for monitoring batteries to insure that the accuracy and reliability of present invention is not compromised because the batteries are wearing out.

Figure 1A:
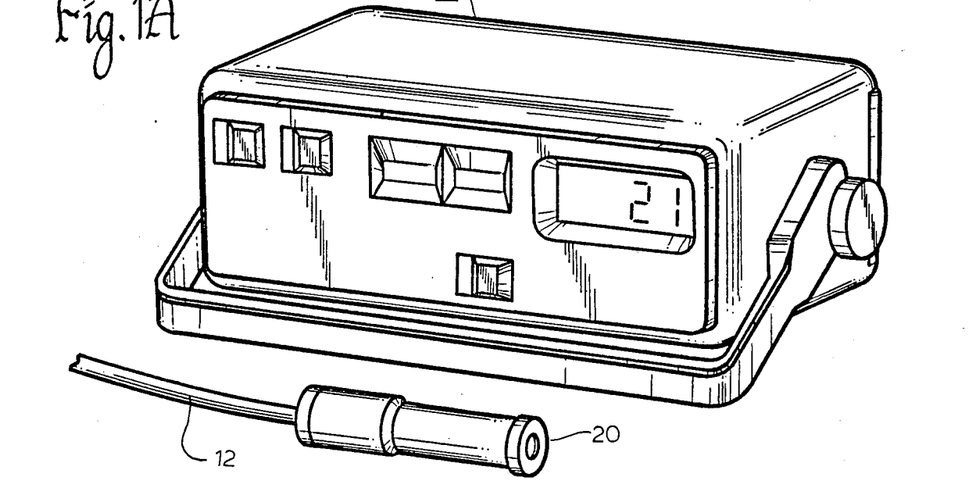
FIG. 1A is a perspective view of the oxygen monitor of the present invention connected to the sensing device.
Figures 1B, 1C, 1D:
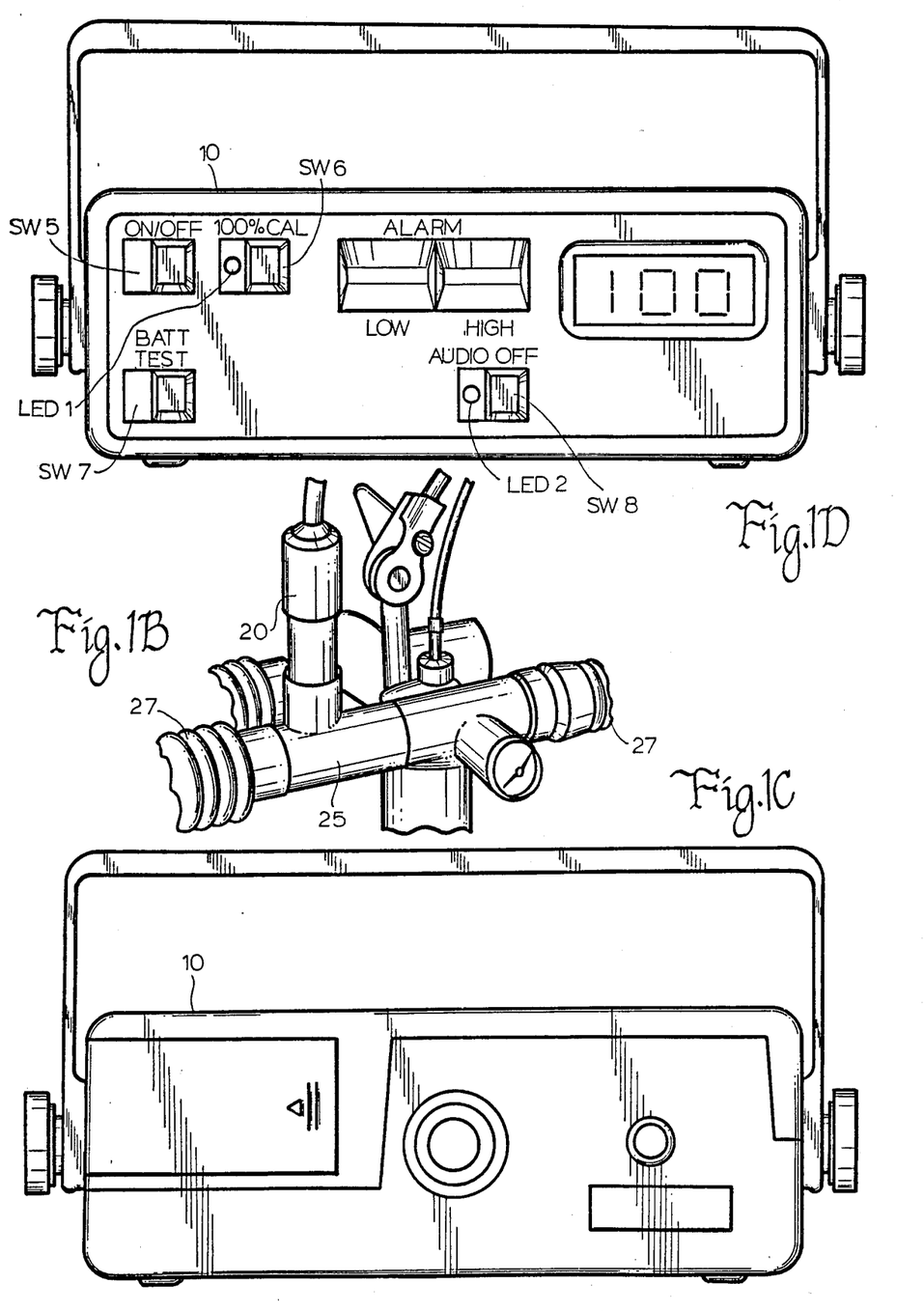
FIG. 1B is a detailed front elevational view of the oxygen monitor.
FIG. 1C is a rear elevational view of the oxygen monitor of this invention.
FIG. 1D is a perspective view of the sensing device interconnected to oxygen hoses typically used in medicine.

Referring now to FIGS. 1A, and 1D the preferred embodiment of the present invention 10 is intended to operate with the sensing device 20 of the type generally described in U.S. Pat. No. 4,367,133, which is incorporated herein by this reference as if fully set forth. The sensing device described in U.S. Pat. No. 4,367,133 is an electrochemical, galvanic type device generally comprising a platinum cathode, a lead anode, an electrolyte solution and a thermistor (none of which are shown), and, creates an electrical current proportional to the percentage of oxygen surrounding the sensing device 20. This electrical current is used by the preferred embodiment of the present invention 10 (hereinafter "the oxygen monitor 10") to display the numerical value of the percentage of oxygen which surrounds the sensing device 20. A long extension cord 12 is used to interconnect the sensing device 20 to the oxygen monitor 10 so that the sensing device 20 can be placed in remote environments which are sealed from open air.

Referring to FIG. 1B, the sensing device 20 is interfit within a "T" coupling 25 which, in turn, is interfit within oxygen lines 27. Thus, the oxygen monitor 10 of FIGS. 1A, 1C and 1D can display the percentage of oxygen which is being used for medicinal or other purposes in an environment sealed from the open air. While used in the area of medicine, the oxygen monitor is an invaluable tool which allows the user to continuously monitor the percentage of oxygen in a gas mixture breathed by the patient, and, will sound an alarm if the percentage of oxygen is outside a physician set range of acceptable oxygen percentages.

1. Overview of the Electronics of the Oxygen Monitor

Figure 2:
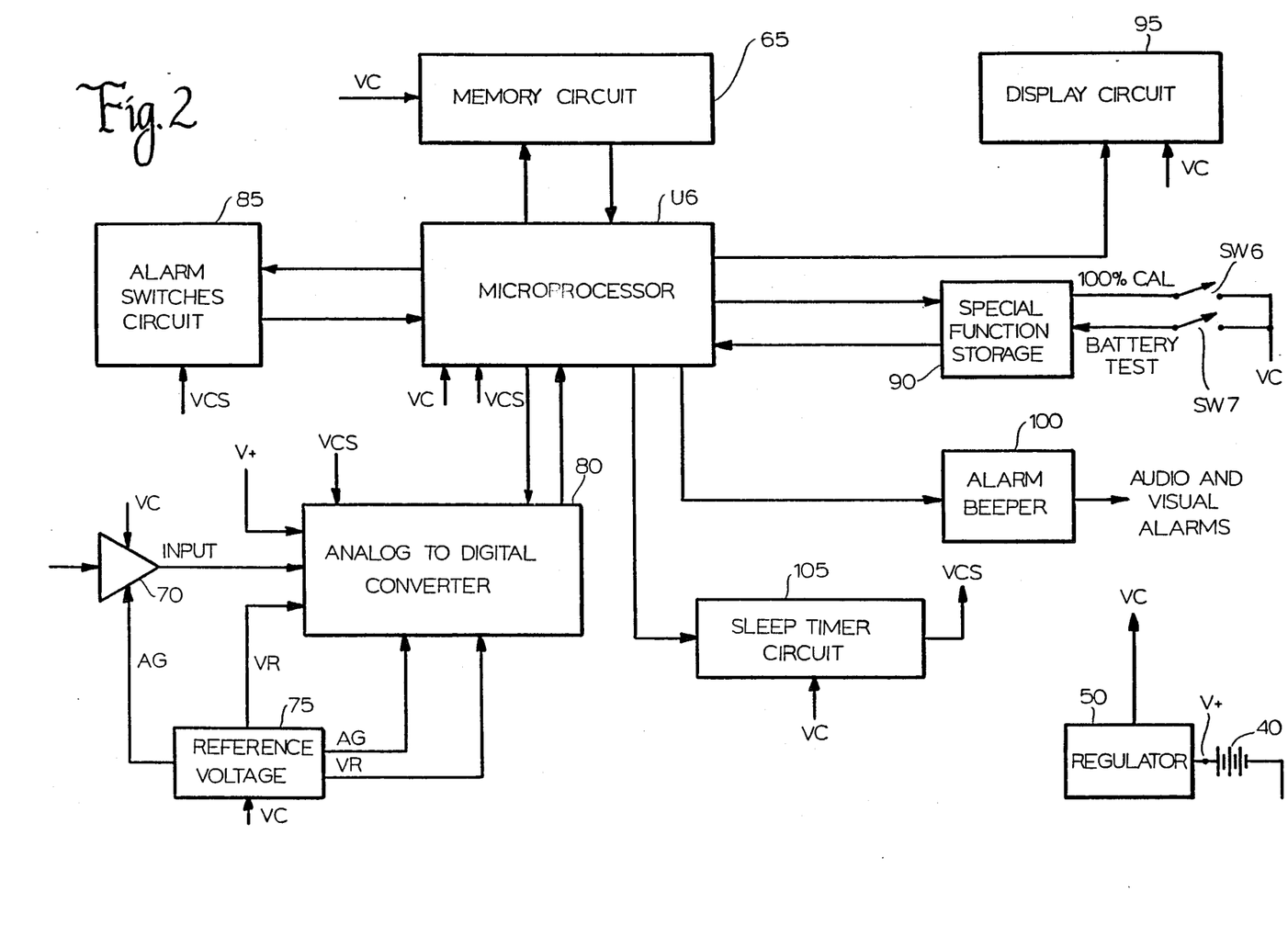
FIG. 2 is an electronic block diagram of the electronics of the oxygen monitor.

Referring to FIG. 2, wherein the block diagram of the electronics of the oxygen monitor 10 is shown. The oxygen monitor 10 is preferably powered by a battery supply 40. The battery supply voltage is regulated by regulator 50 to provide the necessary voltages for the integrated circuits which compose the electronics of the oxygen monitor 10. The heart of the electronics of the oxygen monitor 10 is the microprocessor U6 which uses memory circuit 65 to store its programming.

The sensing device 20 of FIG. 1B is interconnected to the electronics of the oxygen monitor 10 via input circuit 70. In order to inform the microprocessor U6 of the value of a reference voltage and for other purposes, reference voltage circuit 75 creates a reference voltage. The unregulated battery supply voltage (V+), the voltage developed from the sensing device 20 through input circuit 70 and the reference voltage (VR) from reference voltage circuit 75 are each converted to digital signals which are, in turn, transmitted to the microprocessor U6 via analog-to-digital converter circuit 80.

The alarm limits are set by the user by setting the low and high alarm switches of FIG. 1D through alarm switches circuit 85 of FIG. 2 which send the alarm limits to the microprocessor U6. The microprocessor U6 can be prompted by switches SW6 and SW7 together with special function storage circuit 90 to calibrate the oxygen monitor 10 in a one hundred (100%) percent oxygen environment and to display the estimated remaining battery life, respectively. (Each of these functions will be subsequently described in more detail). The oxygen percentage reading, the estimated remaining battery life and other information is displayed through display circuit 95 under the control of the microprocessor U6.

If the oxygen percentage is outside the limits set by the user or if the estimated remaining battery life is less than ten (10) hours, then the microprocessor U6 will cause an audio and visual alarm through alarm beeper circuit 100.

In order to conserve the battery supply 40, the oxygen monitor 10 can be equipped with sleep timer circuit 105 which takes the VC supply and creates a switched VC supply (VCS). By switching the VC supply, the sleep timer circuit 105 powers-down all but the essential microprocessor U6 circuits for about ½ second at the end of each program cycle and then restores power for the next cycle, as will be more fully explained in discussions of the detailed electronic circuitry of the oxygen monitor 10.

2. Basic Operation of Oxygen Monitor

Figure 4A:
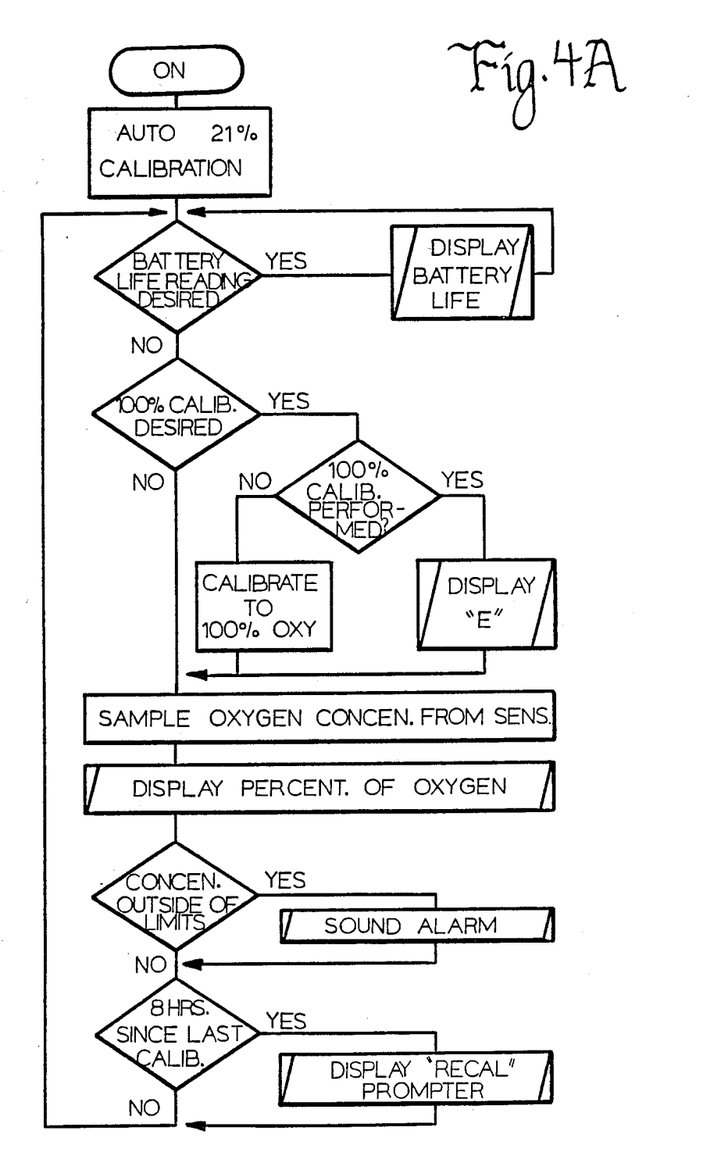
FIG. 4A is an operational flow chart showing the basic operation of the oxygen monitor.

Referring to FIG. 4, the operational flow chart for the oxygen monitor 10 is shown. When the oxygen monitor 10 is initially turned on, it performs an automatic calibration to 21% oxygen (the percentage of oxygen in open air) in order to insure that the readings of oxygen percentage are reasonably accurate. It is important to note that the current from the sensing device 20 typically will vary from day to day and from sensing device 20 to sensing device 20 even in open air which has an entirely stable oxygen percentage. Thus, calibration of the oxygen monitor 10 is important for accurate readings.

Next, the oxygen monitor 10 determines whether there has been a manual request for the estimated battery life. If so, the the estimated battery life is displayed. (A more detailed discussion of the function of monitoring the battery supply 40 of FIGS. 2 and 3D is included under the subtitle of "Battery Supply Monitor Function" below). If not, the oxygen monitor 10 determines whether there has been a manual request for a calibration in a 100% percent oxygen environment. If so, the 100% oxygen calibration is performed unless this step has already been performed after the oxygen monitor 10 was turned on. If this step had already been performed, the oxygen monitor 10 will prohibit the 100% oxygen calibration and will display an -E- to indicate to the user that this step has been performed. The reason for determining whether a 100% oxygen calibration has been performed and prohibiting a second 100% oxygen calculation will be explained when the two point calibration operation is subsequently discussed in detail.

If no 100% oxygen calibration is requested, the oxygen monitor 10 samples the current from the sensing device 20 and displays the calculated percentage of oxygen. Next, the oxygen monitor 10 checks to see if the calculated percentage is outside the alarm limits set by the user. If so, the alarm is sounded. If not, the oxygen monitor 10 then determines whether there has been eight (8) hours since the last calibration. If so, the oxygen monitor 10 displays a user prompt to recalibrate the oxygen monitor 10.

This entire process, except the automatic 21% oxygen calibration, is then performed over and over again until the oxygen monitor 10 is turned off, whereafter the automatic 21% oxygen calibration begins again the entire cycle after the oxygen monitor 10 is again turned on.

3. Two Point Calibration of Oxygen Monitor

Before discussing in detail the two point calibration, it is important to note as previously stated that the current from any given sensing device 20, although always proportional to the percentage of oxygen in the environment, will often produce different amounts of current on different occasions for the same percentage of oxygen. In addition, any two sensing devices 20 will typically produce different currents for the same percentage of oxygen. It is also important to note that the change in current from sensing device 20 is always linear from 0 to 100 percent oxygen when the sensing device 20 is properly functioning. Thus, calibrating the oxygen monitor's 10 reading in open air (21% oxygen), as is performed each time the oxygen monitor 10 is turned on, will insure that the percentage oxygen reading at 21% is accurate.

However, even though the changes in current from the sensing device 20 is always linear from 0 to 100 percent oxyen in the environment, the slope of those linear changes in current can also vary from sensing device 20 to sensing device 20 and from time to time in a single sensing device 20. Therefore, to insure accurate readings from the oxygen monitor 10 over the entire range of possible percentages of oxygen in the environment, a two point calibration has been invented which corrects for offset error conditions and slope error conditions.

Figure 5:
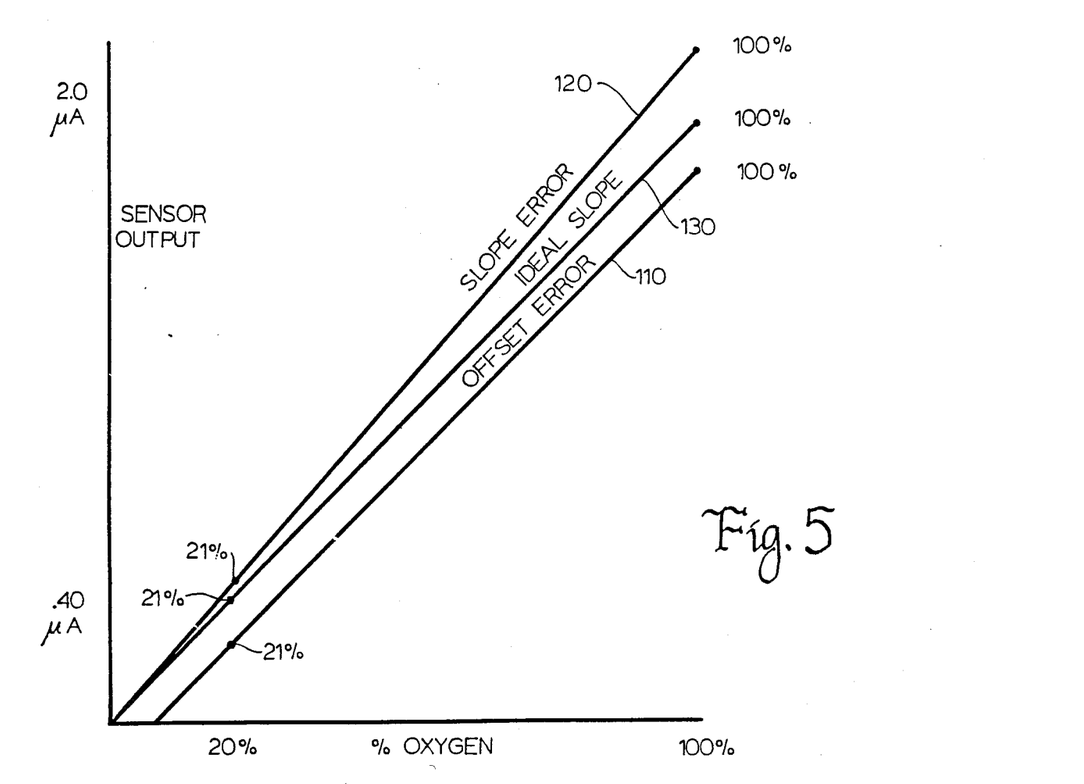
FIG. 5 is a graph of current from the sensing device (vertical axis) against the actual percentage of oxygen in the environment (horizontal axis) to aid in the explanation of slope and offset errors.

Referring to FIG. 5, the novel and unobvious two point calibration feature of the oxygen monitor 10 is graphically described. FIG. 5 is a graph of current from the sensing device 20 (vertical axis) against the actual percentage of oxygen in the environment surrounding the sensing device 20 (horizontal axis). Line 130 shows an ideal corrected slope of the line of changes in current from the sensing device 20 which would allow accurate readings by the oxygen monitor 10 over the entire range of possible oxygen percentages. However, the changes in current from the sensing device 20 are not definable by this ideal corrected line 130 without the novel and unobvious two point calibration.

Typically, the sensing device 20 has a slope error as indicated by line 120 where the changes in current do not allow the ideal slope of line 130. Using a full-scale calibration adjustment, this slope error condition is easily corrected by calibrating the device to 21% oxygen. Since the oxygen monitor 10 "remembers" the correction factor obtained during the 21% calibration, each current reading by the oxygen monitor 10 is then corrected to reflect this slope error. However, if the offset condition exists where the changes in current are only offset from the ideal correct line 130 as indicated in line 110, the sensor output cannot be corrected by calibrating to only 21% oxygen. This is because when the sensor reading is corrected by calibrating to 21% oxygen, only the correction factor is 4.76 times greater (ratio between 21.0% and 100%) at 100% oxygen than at 21%, which will correct for a slope error, but not an offset error.

In order to correct for offset errors as well as slope errors, the two point calibration has been developed. The second point of calibration was chosen as 100% oxygen because pure oxygen is available to the user and it is the only environment (other than open air) where the user can be sure of the percentage of oxygen present in the environment.

In order to complete the 100% oxygen calibration, the user installs the sensing device 20 into an airtight interconnection with a pressurized container (unshown) of pure oxygen, and, turns on the pressurized container to fill the sealed environment with pure oxygen. Next, the user pushes the 100% calibration switch (SW6 of FIGS. 1B, 2 and 3C) on the oxygen monitor 10.

The oxygen monitor 10 corrects its current readings of current from the sensing device 20 to reflect the offset error, if any, in addition to the slope error. Thusly, the oxygen monitor 10 corrects for the two known error conditions of the sensing device 20 to insure accurate readings over the entire range of possible oxygen percentages.

The reason why the oxygen monitor 10 prohibits a second 100% oxygen calibration after the oxygen monitor 10 has been turned on is that for optimum accuracy and reliability, the 21% oxygen calibration must be performed at approximately the same time as the 100% oxygen calibration. If the two calibrations are not performed at about the same time, then any slope and/or offset errors in the current from the sensing device 20 which occurred after the 21% oxygen calibration but before the delayed 100% oxygen calibration would cause the oxygen monitor to read inaccurately. The oxygen monitor 10 requires the user to turn it off before recalibrating, thus requiring that the automatic 21% oxygen calibration be performed before and at approximately the same time as the 100% oxygen calibration.

4. Details of Calibration Procedure

Figure 3A:
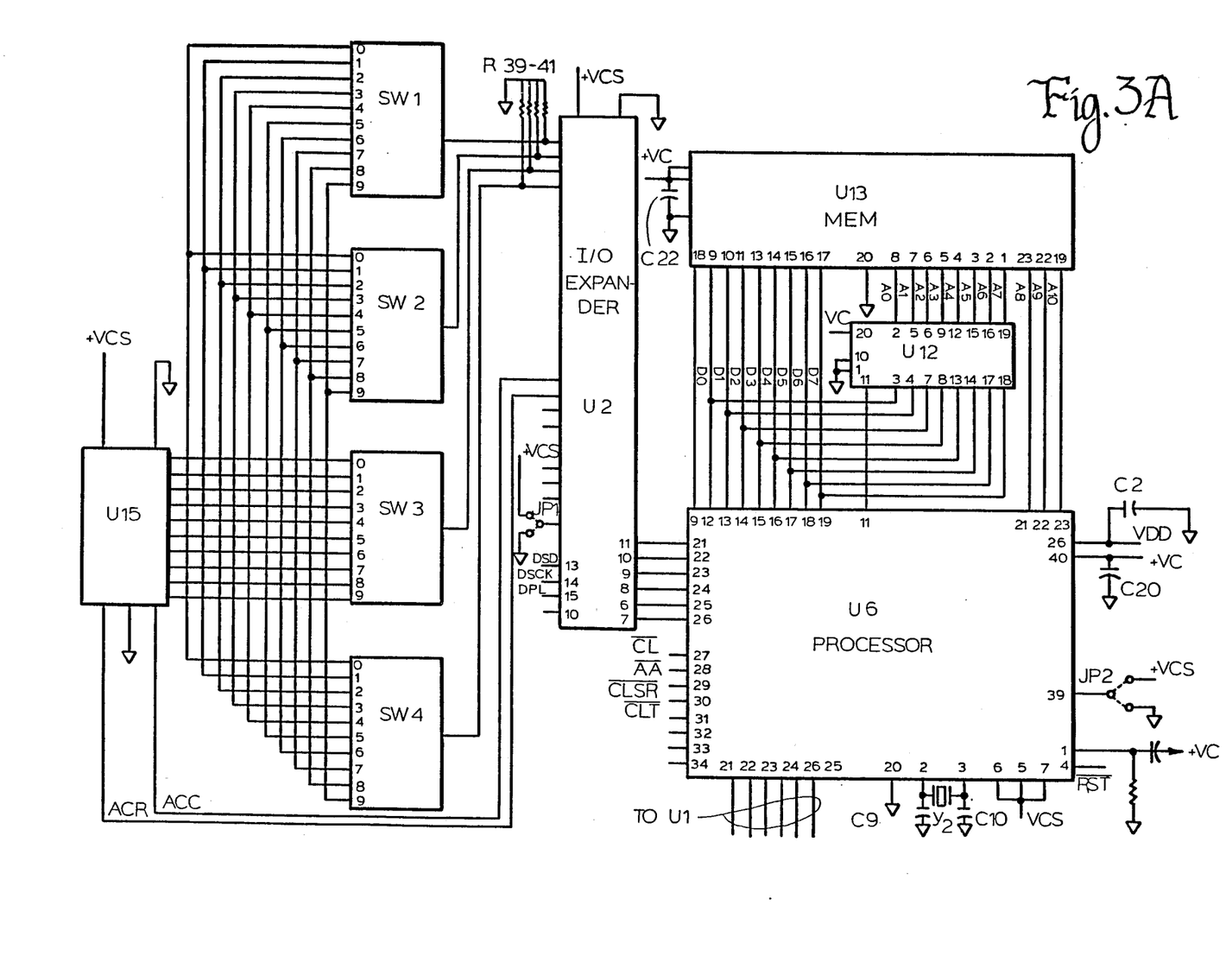
FIG. 3A is a detailed electronic schematic diagram of the microprocessor, memory circuit and alarm switching circuit of the oxygen monitor.
Figure 4B:
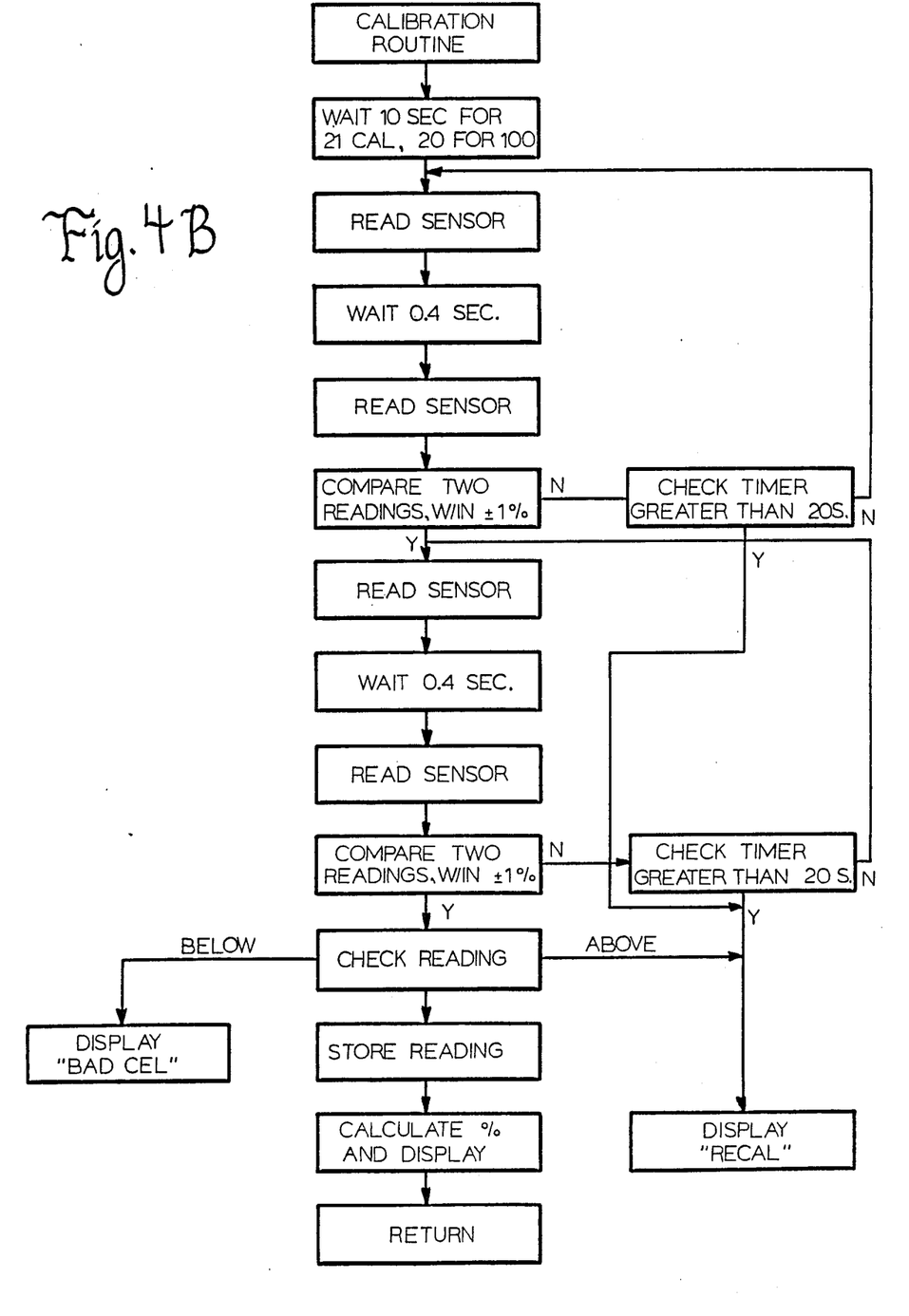
FIG. 4B is a flow chart showing the basic manner for calibrating the oxygen monitor.

Referring to FIG. 4B, the procedure for the microprocessor U6 (FIGS. 2 and 3A) of the oxygen monitor 10 for both the 21% and 100% oxygen calibrations is shown. After a calibration procedure is begun, the microprocessor U6 will wait 10 seconds if the 21% oxygen calibration is to be performed and 20 seconds if the 100% oxygen calibration is to be performed. Next, the current from the sensing device 20 is read and then the microprocessor waits 0.4 seconds and reads the current from the sensing device 20 again. Next, the two readings from the sensing device 20 are compared. If the two readings are within plus or minus 1%, then this process of two readings interrupted by a wait for 0.4 seconds and the comparison of the readings is repeated. If during any of these two double reading cycles the readings vary more than plus or minus 1%, then the microprocessor U6 checks to see if 20 seconds has gone by during the cycles of two double readings. If so, the display circuit 95 (FIGS. 2 and 3A) is made to indicate that the oxygen monitor 10 needs to be recalibrated, and the calibration procedure is terminated. The user is instructed not to use the oxygen monitor 10 until it is recalibrated at the 21% oxygen and 100% oxygen points.

If the reading from the sensing device 20 is stable enough to pass both double reading cycles, then the reading is checked to see if it is below a predetermined limit which indicates that the sensing device 20 is defective. If the reading is below this predetermined limit, the display circuit 95 is made to indicate to the user that the sensing device 20 is defective and must be replaced before using the oxygen monitor 10 further.

Next, the reading is checked to see if it is above a predetermined limit which usually indicates that the sensing device 20 was not placed in the proper gas during either the 21% or the 100% calibration. If the reading is above the predetermined limit, then the display circuit 95 is made to indicate to the user that the oxygen monitor 10 needs to be recalibrated before further use.

If the reading from the sensing device 20 is stable and within the two predetermined limits previously described, then the reading is stored in the microprocessor U6, the percentage of oxygen is calculated in microprocessor U6 and displayed by the display circuit 95, and, the calibration procedure is terminated until next time.

5. Battery Supply Monitor Function

Referring again to FIG. 2, the battery supply 40 monitor function begins by allowing the battery supply voltage to be monitored by the microprocessor U6 via the analog to digital converter circuit 80. Stored in the programming for the microprocessor U6 is information on the average discharge time for the recommended battery supply 40. This average discharge time information is compared to the actual battery supply voltage and an estimated remaining battery life is calculated periodically by microprocessor U6. Preferably, when the recommended battery supply 40 (preferably 6 type AA alkaline batteries) has less than 58 remaining estimated hours of life, the microprocessor U6 causes the display circuit 95 to indicate that a low battery condition exists and the battery supply 40 must be replaced, but the oxygen monitor 10 is in no immediate danger of becoming inaccurate because of the low battery supply 40.

The battery supply 40 monitor function will also cause the display of a low battery condition and disable the display of oxygen percentages when the dangerously low estimated battery life of 10 hours is calculated. Thus, the user will not receive inaccurate readings because the battery supply 40 is about to wear out.

The battery supply 40 monitor function also includes a battery test switch SW7 which allows the user to cause the display of the estimated remaining battery life by the microprocessor U6 at any time.

7. Detailed Description of the Electronics of the Oxygen Monitor

Figure 3B:
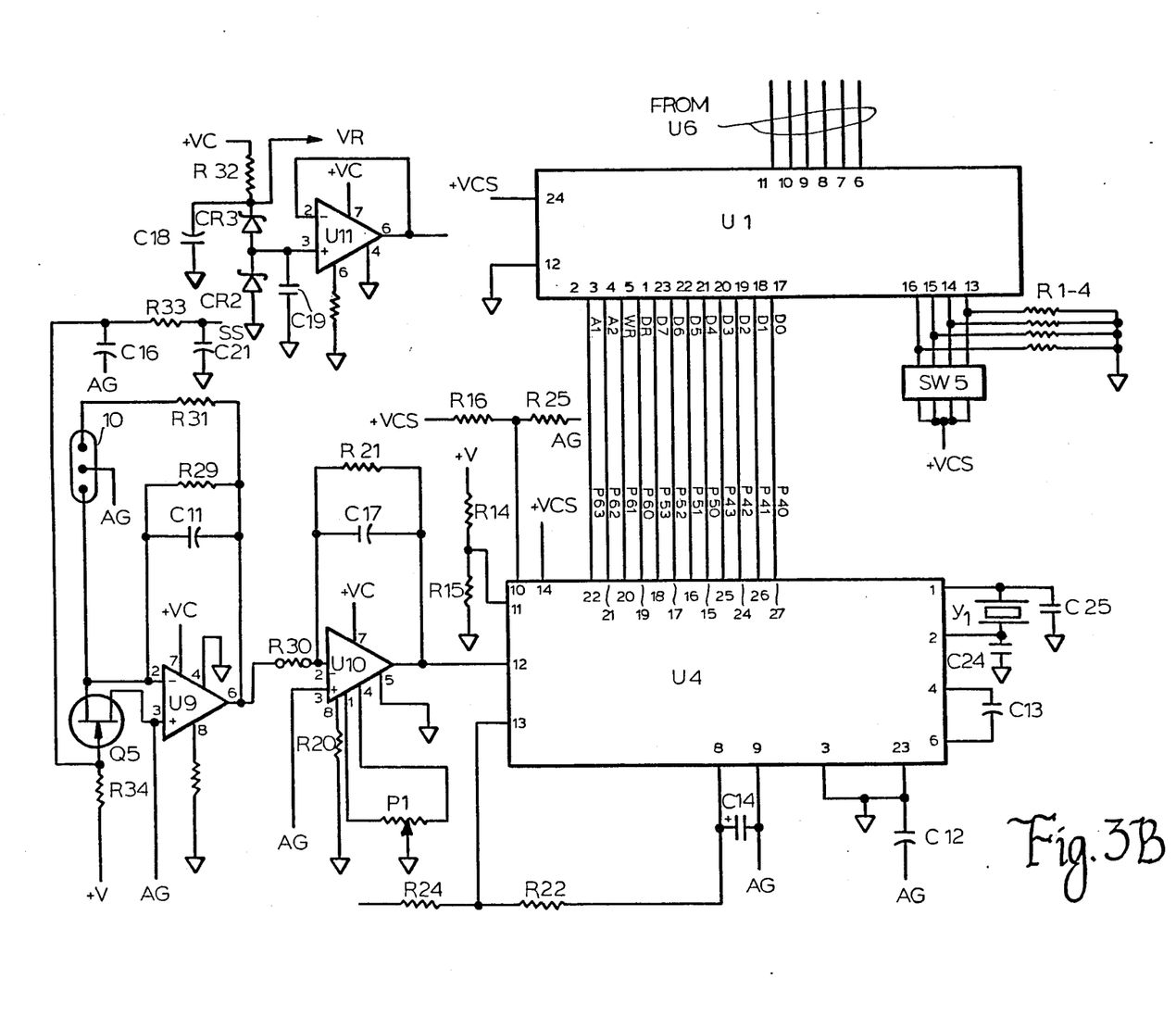
FIG. 3B is a detailed electronic schematic diagram of the analog to digital converter circuit, reference voltage circuit, and input circuit of the oxygen monitor.
Figures 3C, 3E:
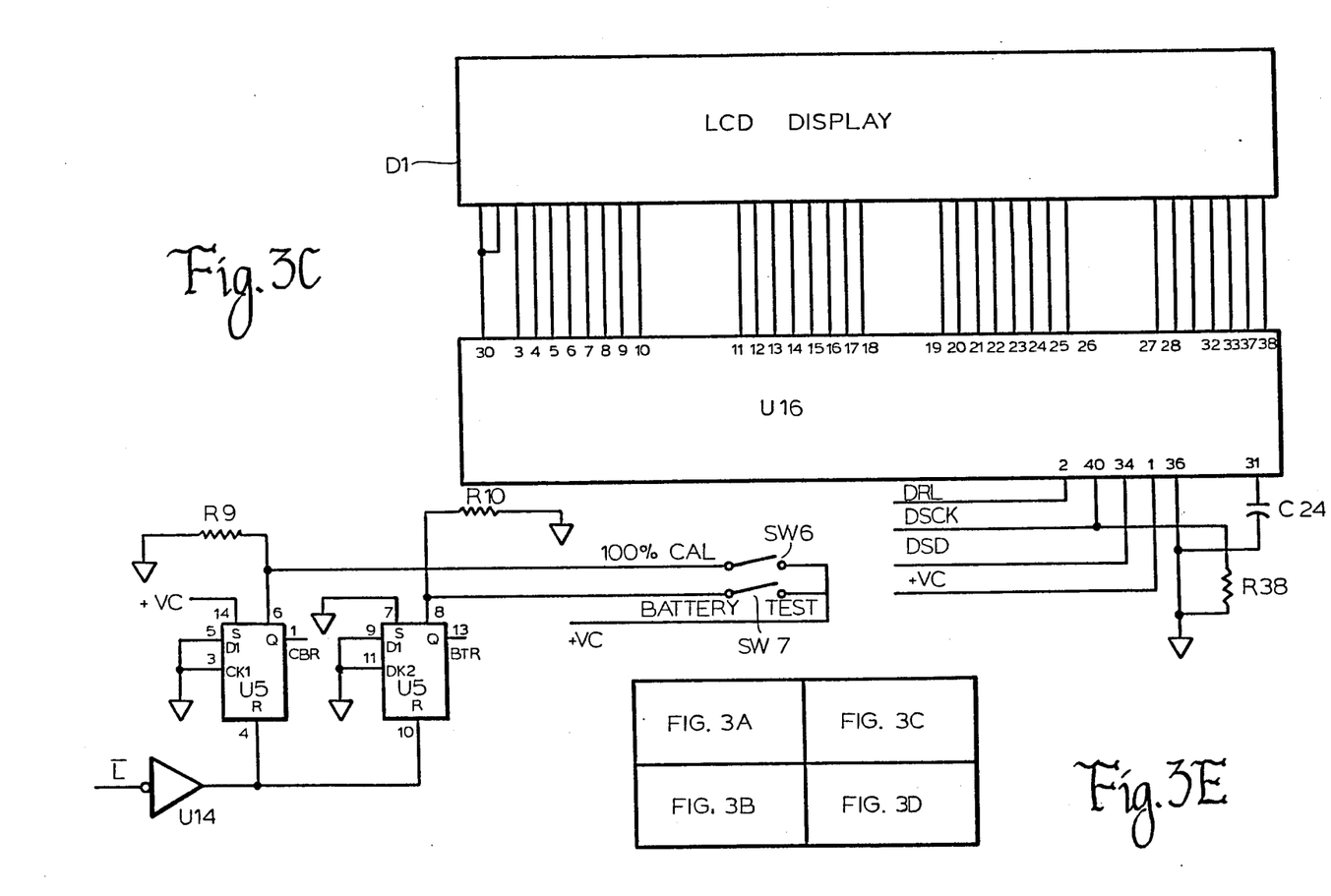
FIG. 3C is a detailed electronic schematic diagram of the display circuit and the special function storage circuit of the oxygen monitor.
FIG. 3E is a graphic depiction of the manner that FIG. 3A through 3D are to be placed to create a detailed electronic schematic diagram of the entire oxygen monitor.
Figure 3D:
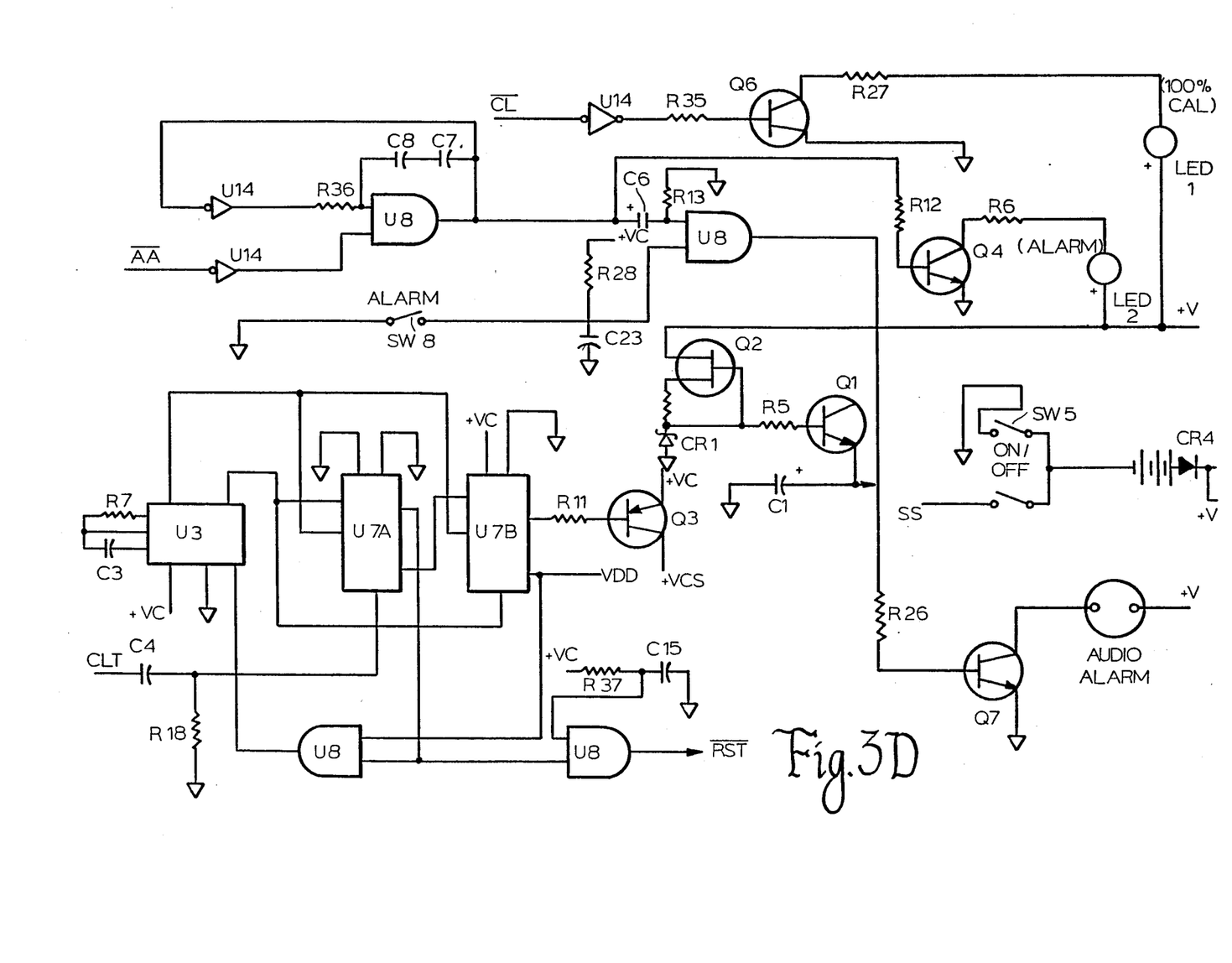
FIG. 3D is a detailed electronic schematic diagram of the alarm beeper circuit, regulator circuit and sleep timer circuit of the oxygen monitor.

Referring momentarily to FIG. 3E, a map of how to assemble FIGS. 3A through 3D into a single complete detailed circuit diagram for the electronics of the oxygen monitor 10 is shown.

Referring now to FIG. 3A, microprocessor U6 is preferably a UPD 80C35 8 bit microprocessor with 27 I/O ports, 1K/8 ROM and 64/8 RAM memories, manufactured by NEC corporation. The microprocessor U6 is preferably run at 6 Mhz with the aid of 6 Mhz crystal Y2. Memory circuit 65 preferably comprises EPROM U13 and 74C373 octal transparent latch with 3-state output buffers U12. Alarm switches circuit 85 preferably comprises thumbswitches SW1 through SW4, CD 4017 decade counter/driver U15, and 82C43 I/O expander U2.

Referring now to FIG. 3B, analog to digital converter circuit 80, input circuit 70 and reference voltage circuit 75 are shown in detail. Analog to digital converter circuit 80 preferably comprises a UPD 7002C analog input, MUX, A/D converter U4 manufactured by NEC corporation and a 82C43 I/O expander U1. U4 is preferably run at 3 Mhz with the aid of 3 Mhz crystal Y1. Reference voltage circuit 75 preferably comprises an LM 4250 programmable operational amplifier U11, zener diode CR2, zener diode CR3 and associated components. Input circuit 70 preferably comprises two LM 4250 programmable operational amplifiers U9 and U10, transistor Q5 and associated components. U9 converts the sensing device's 20 current output to a negative voltage. This negative voltage is then amplified and inverted to a positive voltage by U10. Transistor Q5 is used to short-out the sensing device 20 when the oxygen monitor 10 is shut off to allow the sensing device 20 to be at a peak response at time of power-up by placing a small load on it at all times.

Referring now to FIG. 3C, display circuit 95 preferably comprises a UA 438 CMOS/LSI serial input LCD display drive U16 and a custom LCD display D1. The only way that display D1 differs from a standard LCD display is that it can display the prompts "LOW BATT", "RECALIB", "BAD CELL", "SERVICE", "Hr" and "%" with commands from microprocessor U6. Special function storage circuit 90 preferably comprises switches SW6 and SW7, CD 4013 dual D flip-flop U5, part of CD 4069 hex inverter U14 (all shown in FIG. 3C), transistor Q6, LED1 (shown only in FIG. 3D), and associated components. When the 100% oxygen calibration switch SW6 is depressed, LED1 will light under the control of the microprocessor U6.

Referring to FIG. 3D, alarm beeper circuit 100 preferably comprises a portion of CD 4069 hex inverter U14, CD4081 quad 2-input AND buffered B series gate U8, transistor Q4 and alarm LED2. The audio and visual alarm can be disabled by the user using switch SW8. Regulator circuit 50 preferably comprises JFET-N channel Q2, transistor Q1, zener diode CR1 and associated components.

Sleep timer circuit 105 preferably comprises CD 4060 14 stage ripple carry binary counter U3, CD 4013 dual D flip-flop U7a and U7b, transistor Q3 and one half of CD 4081 quad 2-input AND buffered B series gate U8. The sleep timer circuit 105 powers-down all but the essential microprocessor U6 circuits for about ½ second at the end of each program cycle to preserve power. This is achieved by forcing CLT momentarily high. This resets flip-flop U7A, starting the ½ second timer U3 and resetting microprocessor U6. About 6 ms thereafter, U7B is set causing both VCS and VDD to drop, leaving only essential power for the microprocessor U6 on. Power remains off for about ½ second at which time U3 times out and resets U7B, restoring VCS and VDD, and 6 ms later resets U7A, clearing the microprocessor U6 reset line. The microprocessor U6 will run another program cycle and then repeat the sleep cycle.

The oxygen monitor 10 is programmed to operate with the above described elements in a conventional manner using well known machine language programming techniques.

In the embodiment of the oxygen monitor 10 disclosed, the following component have been found to operate properly:

| | |
|---|---|
| R7, R21, R39, R40 R41, R42, R38 | 100K ohms, ¼ watt, 1% |
| R18, R37 | 10K ohms, ¼ watt, 5% |
| R1-R4 | 100K ohms, ¼ watt, 5% |
| R17, R34, R19, R9, R10, R20, R23, R13 | 1 Meg ohm, ¼ watt, 5% |

-continued

| | |
|---|---|
| R28, R36, R33, R16 | 562K ohm, ¼ watt, 1% |
| R32 | 7.5K ohm, ¼ watt, 1% |
| R14, R22, R24 | 200K ohm, ¼ watt, 1% |
| R5 | 1K ohm, ¼ watt, 5% |
| R31 | 39.2K ohm, ¼ watt, 1% |
| R29 | 681K ohm, ¼ watt, 1% |
| R8 | 1K ohm, ¼ watt, 1% |
| R12, R26, R35 | 3.9K ohm, ¼ watt, 5% |
| R30 | 45.3K ohm, ¼ watt, 1% |
| R6, R26 | 220K ohm, ¼ watt, 5% |
| R15 | 63.4K ohm, ¼ watt, 1% |
| R11 | 18K ohm, ¼ watt, 5% |
| R25 | 84.5K ohm, ¼ watt, 1% |
| C5 | 10 Mfd, 16–35 WVDC, 10% |
| C2, C11, C17 | 14 Mfd, 100 WVDC, 10% |
| C20, C21, C22 | .01 Mfd, 100 WVDC, 10% |
| C4, C16 | |
| C6, C7, C8, C12 | 1 Mfd, 16–35 WVDC, 20% |
| C14, C15, C18, C19, C13 | .004 Mfd, 100 WVDC, 10% |
| C23 | 33 Mfd, 16–35 WVDC, 10% |
| C1 | 100 Mfd, 25 WVDC |
| C3 | 560 pfd, 1000 WVDC, 10% |
| C9, C10 | 22 pfd, 1000 WVDC, 10% |
| C24 | 47 pfd, 1000 WVDC, 10% |
| CR1 | 5.6 v Zener diode |

The above described embodiment of the present invention is merely descriptive of its principles and is not to be considered limiting. The scope of this invention shall instead be determined from the scope of the following claims and their equivalents.

What is claimed is:

1. In a condition sensing and display apparatus including (1) a sensor means for producing an electrical signal proportional to a sensed condition, (2) means for converting the electrical signal from the sensor means to digital signals, first switch means for initiating and terminating operation of the apparatus and second switch means for initiating calibration at an offset condition, and (3) means responsive to the digital signals for displaying a numerical value associated with the sensed condition, an improvement comprising:

first calibration means responsive to said first switch means for automatically calibrating the display of the numerical value associated with sensed condition to a numerical value associated with the sensed condition in a normal ambient environment, while the sensor means is within the normal ambient environment when said first switch means is activated to initiate operation of the apparatus; and second calibration means responsive to said second switch means for calibrating the display of the numerical value of the sensed condition to a numerical value associated with the sensed condition in a known offset environment which is different than the normal ambient environment, while the sensor means is in the known offset environment;

the calibration of the display of the numerical value associated with the sensed condition in the normal ambient environment and in the known offset environment aiding in protection from a slope error condition and an offset error condition in the display of the numerical value associated with the sensed condition.

2. The condition sensing and display apparatus in accordance with claim 1 further including means for controlling said display so as to indicate that the apparatus is performing the calibration in the normal ambient environment and means for controlling said display indicating that the apparatus is performing the calibration in the known offset environment.

3. The condition sensing and display apparatus in accordance with claim 1 further including means for controlling said display so as to indicate a need to recalibrate the apparatus when the electrical signal from the sensor means fails to possess a predetermined characteristic.

4. The condition sensing and display apparatus in accordance with claim 1 further including means for controlling said display so as to indicate a malfunction of the sensor means when the electrical signal from the sensor means fails to possess a predetermined characteristic.

5. The condition sensing and display apparatus in accordance with claims 3 or 4 in which (1) the sensed condition is the percentage of oxygen in a selected environment, (2) the sensor means comprises an electrochemical device comprising a platinum cathode, a lead anode, an electrolyte solution and a thermistor for creating an electrical current proportional to the percentage of oxygen, (3) the predetermined characteristic for indicating the need for recalibration comprises a high electrical current limit from the electrochemical device, indicative that the recalibration is needed for the apparatus to accurately measure the percentage of oxygen in the selected environment, and (4) the predetermined characteristic for indicating the malfunction of the electrochemical device comprises a low electrical current limit from the electrochemical device, indicative that the electrochemical device is malfunctioning.

6. The condition sensing and display apparatus in accordance with claim 1 further including:

means for determining whether the apparatus has been recalibrated within the predetermined minimum recalibration time period;

means for indicating that there is a need to recalibrate the apparatus in the event that the predetermined recalibration time period has elapsed and no attempt has been made to recalibrate the apparatus; and, means for resetting the measuring of the predetermined recalibration time period when there has been an attempt to recalibrate the apparatus within the predetermined recalibration time period.

7. The condition sensing and display apparatus in accordance with claim 1 further including means for disabling said second calibration means for calibrating at known offset environment after said second switch means has been actuated, whereby a subsequent calibration at an offset condition is prohibited until operation of the apparatus is successively terminated and initiated by further actuating said first switch means.

8. The condition sensing and display apparatus in accordance with claim 7 further including means for disabling said first calibration means for calibrating at normal ambient environment after said first switch means has been actuated, whereby a subsequent calibration at normal ambient environment is prohibited until operation of the apparatus is successively terminated and initiated by further actuating said first switch means.

9. The condition sensing and display apparatus in accordance with claim 1 wherein said first and second switch means each comprises manual switch means, wherein said first calibration means includes switching means responsive to said first switch means for controlling calibration in a normal ambient environment, and wherein said second calibration means includes switching means responsive to said second switch means for controlling calibration in a known offset environment.

10. In a method for sensing and displaying a condition including the steps of (1) sensing the condition and producing an electrical signal proportional to the sensed condition, (2) converting the electrical signal to digital signals, and (4) displaying a numerical value associated with the sensed condition responsive to the digital signals, an improvement comprising the steps of:

first calibrating the display of the numerical value associated with the sensed condition to a numerical value associated with the sensed condition in a normal ambient environment, while sensing the normal ambient environment;

secondly calibrating the display of the numerical value of the sensed condition to a numerical value associated with the sensed condition in a known offset environment which has a greater numerical level of the condition senses than the normal ambient environment, while sensing the known offset environment, and disabling the second calibrating step until the first calibrating step is repeated;

the steps of calibrating the display of the numerical value associated with the sensed condition in the normal ambient environment and in the known offset environment aiding in protection from a slope error condition and an offset error condition in the displaying of the numerical value of the sensed condition.

11. The improved method for sensing and displaying a condition in accordance with claim 10 further including the steps of:

initiating sensing operation;

indicating when recalibration is required;

indicating that the step of calibrating in the normal ambient environment is being performed when so calibrating;

indicating that the steps of calibrating in the known offset environment is being performed when so calibrating; and thereafter accurately indicating the condition sensed.

12. The improved method for sensing and displaying a condition in accordance with claim 10 further including the step of indicating a malfunction in sensing the condition when, despite calibration, the electrical signal fails to possess a predetermined characteristic.

13. The improved method for sensing and displaying a condition in accordance with claim 10 further including the steps of:

measuring a predetermined calibration time period;

determining whether the steps of calibrating in the normal ambient environment and the known offset environment have been performed within the predetermined recalibration time period;

indicating that there is a need to perform the calibration steps in the normal ambient environment and in the known offset environment in the event that the predetermined recalibration time period has elapsed and no attempt has been made to perform the calibration steps in the normal ambient environment and in the known offset environment; and, resetting the measuring of the predetermined recalibration time period when there has been an attempt to perform the steps of calibrating in the normal ambient environment and the known offset environment within the predetermined recalibration time period.

* * * * *